United States Patent [19]

Ito et al.

[11] Patent Number: 4,633,706
[45] Date of Patent: Jan. 6, 1987

[54] SYSTEM FOR MEASURING AMOUNT OF PARTICULATES EXHAUSTED FROM VEHICLE ENGINE

[75] Inventors: Seitoku Ito; Shigeo Iwashita, both of Okazaki; Sigeru Kamiya, Chiryu; Hiroshi Noguchi, Gotenba, all of Japan; Nobuhisa Mori, Ann Arbor, Mich.

[73] Assignees: Nippon Soken, Inc.; Toyota Jidosha Kabushiki Kaisha, both of Toyota, Japan

[21] Appl. No.: 666,856

[22] Filed: Oct. 31, 1984

[30] Foreign Application Priority Data

Nov. 1, 1983 [JP] Japan .................................. 58-203641

[51] Int. Cl.$^4$ .......................................... G01N 15/06
[52] U.S. Cl. ....................................................... 73/28
[58] Field of Search ............ 73/23, 28, 863.12, 863.23, 73/863.31; 55/270; 123/440

[56] References Cited

U.S. PATENT DOCUMENTS

| 3,817,100 | 6/1974 | Anderson et al. | ................ 74/864.34 |
| 4,257,258 | 3/1981 | Bovenlander | ............................. 73/23 |
| 4,361,028 | 11/1982 | Kamiya et al. | .......................... 73/28 |
| 4,386,534 | 6/1983 | Englund et al. | ................. 73/863.12 |

Primary Examiner—Stephen A. Kreitman
Attorney, Agent, or Firm—Cushman, Darby & Cushman

[57] ABSTRACT

A system for measuring amounts of particulates exhausted from a vehicle internal combustion engine, such as a diesel engine, has a dilution tunnel into which exhaust gas is introduced and mixed with and diluted by clear air. One part of the diluted gas is introduced into a first sampling arrangement in which a first filter is provided for collecting particulates of dry soot and another part of the diluted gas is introduced into a second sampling arrangement in which a second filter is provided for collecting particulates of soluble organic fraction (SOF). The amounts of dry soot and SOF are calculated in a real time manner in accordance with the pressure drops across the filters on the basis of the time differential of the signals output from pressure transducers provided for each filter.

3 Claims, 6 Drawing Figures

SYSTEM FOR MEASURING AMOUNT OF PARTICULATES EXHAUSTED FROM VEHICLE ENGINE

BACKGROUND OF THE INVENTION

1. Field of the Invention

The present invention relates to a system for measuring in real time amounts of dry soot (e.g., carbon particulates) and a soluble organic fraction (referred hereinafter to as an SOF) which are contained in an exhaust gas from a diesel engine.

2. Description of the Prior Art

There is a tendency for vehicles equipped with diesel engines to increase in number because of the better fuel consumption rate of this type of engine compared with a gasoline engine. However, diesel engines exhaust larger amounts of particulates than those discharged by gasoline engines. The exhausted particulates are a serious problem from the viewpoint of environmental pollution. For this reason, the governments of some countries, such as the United States of America, are inclined to provide severe regulations concerning the quantities of particulates exhausted from diesel engines. Under these circumstances, it is particularly important to determine the particulate exhaust characteristics of vehicles and, more particularly, the particulate exhaust of each vehicle, which varies from moment to moment.

The particulates exhausted from the diesel engine are classified as dry soot and SOF. It is considered that the SOF is more harmful than the dry soot for human health, because the former may include a carcinogenic substance. Therefore, there is a strong demand that the amount of SOF in the exhausted gas be estimated separately from the amount of dry soot therein.

A conventional measurement to determine the amount of dry soot and SOF in the exhausted gas is performed in the following manner: Particulates in an exhaust gas are collected by a filter. The temperature and humidity of the collected particulates are controlled and the particulates are weighed by a chemical balance, thereby determining the concentration of the total particulates. Then, the SOF is extracted by the Soxhlet extraction method from the particulates deposited on the filter and the residue is weighed to determine the concentrations of dry soot and SOF. However, this operation requires a long time to determine the concentrations of dry soot and SOF. Therefore, it is very difficult to determine the rapidly changing concentrations as time passes; which is necessary for continuously regulating the exhaust gas from the diesel engine in a real time manner.

On the other hand, in U.S. Pat. No. 4,361,028, there is proposed a real time system for measuring particulates exhausted from a vehicle internal combustion engine by utilizing a so-called "dilution sampling method". However, according to this system, the dry soot and the SOF cannot be separately measured but are determined as a total amount.

SUMMARY OF THE INVENTION

The present invention has been made in consideration of the above situation, and provides a system for measuring an amount of particulates exhausted from a vehicle engine in such a manner that the concentrations of dry soot and SOF contained in the exhaust gas can be separately measured in a real-time manner.

The above object of the present invention is achieved by a system for measuring the amount of particulates of dry soot and soluble organic fractions contained in exhaust gas from an internal combustion engine. The system comprises a dilution tunnel in which the exhaust gas is mixed with and diluted by a large amount of clean air, a blower means for sucking the exhausted gas and the clean air into the mixed section and discharging the diluted gas therefrom, and means for detecting the amount of particulates in the diluted gas.

The system is improved according to the present invention so that the means for detecting the amount of particulates in the diluted gas comprises first and second arrangements for detecting the amounts of dry soot and soluble organic fractions, respectively. The first arrangement comprises a first sampling pipe for extracting one part of the diluted gas from the dilution tunnel, a first sampling pump for flowing the diluted gas through the first sampling pipe, a first filter for depositing the dry soot on the first filter, a first heating means disposed in the upstream region in the first sampling pipe for heating the diluted gas taken in the first sampling pipe, a first pressure transducer for converting a value of a pressure drop across the first filter to an electrical signal, and a first processor for calculating the amount of dry soot in the exhaust gas in accordance with a differential value of the pressure drop output from the first pressure transducer as a function of time.

The second arrangement comprises a second sampling pipe for extracting another part of the diluted gas from the dilution tunnel, a second sampling pump for flowing the diluted gas through the second sampling pipe, an additional filter of a relatively large size for depositing the dry soot on the additional filter, a second heating means disposed in the upstream region in the second sampling pipe for heating the diluted gas taken in the second sampling pipe, a second filter disposed downstream of the additional filter for depositing the soluble organic fraction on the second filter, a second pressure transducer for converting a value of a pressure drop across the second filter to an electrical signal, and a second processor for calculating the amount of soluble organic fraction in the exhaust gas in accordance with a differential value of the pressure drop output from the second pressure transducer as a function of time.

Preferably, the second arrangement is provided with a cooling pipe between the additional filter and the second filter for condensing the soluble organic fraction in the second arrangement.

Further, it is preferable that temperature detecting means are provided directly upstream of the first and second filters, respectively, for correcting the pressure drops across the first and second filters caused by the heating of the diluted gas.

BRIEF DESCRIPTION OF THE DRAWINGS

The present invention will be described in detail with reference to the drawings illustrating the preferred embodiments, in which.

DESCRIPTION OF THE PREFERRED EMBODIMENTS

Figure 1:
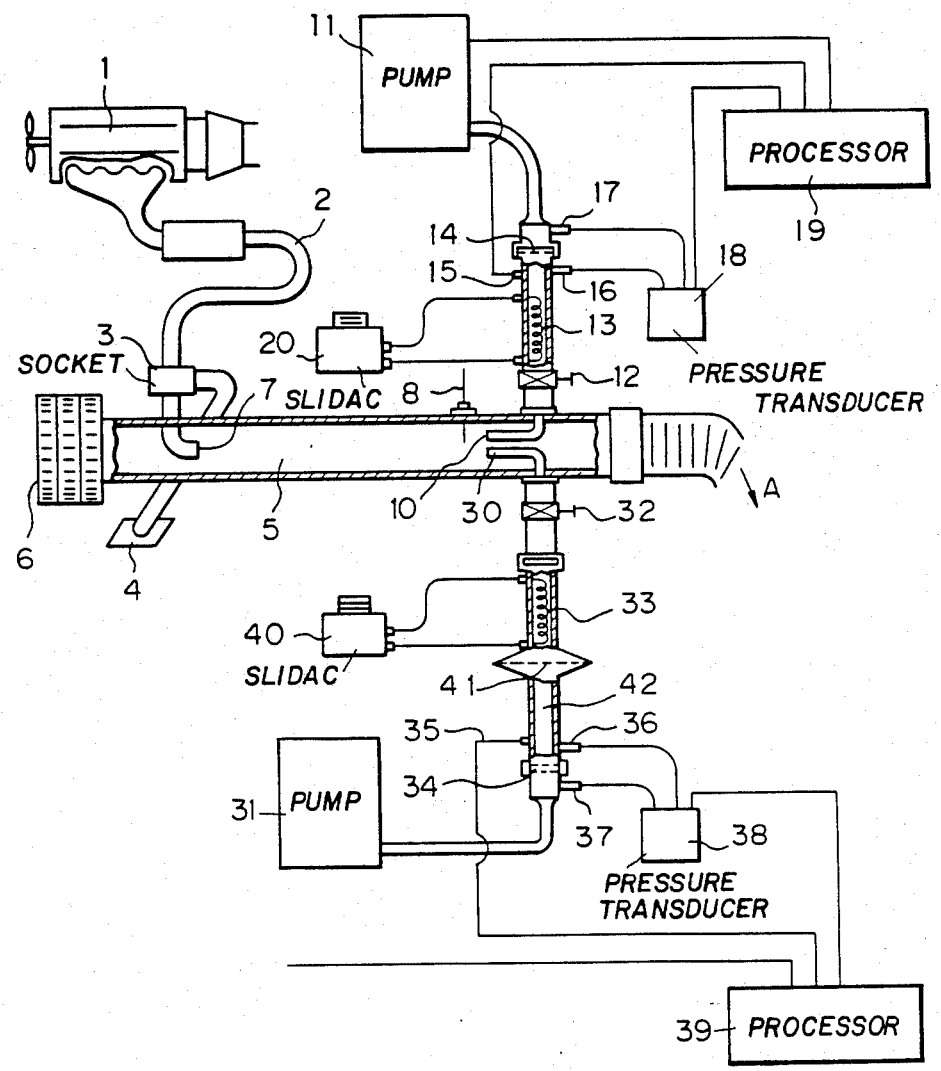
FIG. 1 shows a system configuration, part of which is illustrated as a sectional view according to an embodiment of the present invention.

FIG. 1 shows a first embodiment of the present invention. Referring to FIG. 1, an exhaust pipe 2 extending from a diesel engine 1 is branched into two pipes at a socket 3. One branch pipe is connected to an exhaust port 4, and the other branch pipe 7 communicates with a dilution tunnel 5. Therefore, the exhaust gas from the engine is branched at the socket 3 in such a manner that the main part of the exhaust gas is exhausted from the exhaust port 4 and the residual part is supplied to the dilution tunnel 5 through the pipe 7.

The dilution tunnel 5 serves to mix air supplied from an air intake port 6 with the exhaust gas supplied from the branch pipe 7 of the exhaust pipe 2. A gas mixture obtained by mixing the exhaust gas and air is withdrawn by a root blower (not shown) and flows at a constant speed along the tunnel 5 in the direction indicated by arrow A. A thermometer 8 is disposed midway in the dilution tunnel 5 to detect a temperature in the tunnel. Distal ends of first and second sampling pipes 10 and 30 are aligned parallel to each other in the dilution tunnel 5 for receiving the diluted gas mixture and, respectively, detecting the amounts of dry soot and SOF contained in the exhaust gas.

A first sampling pump 11 is connected to the downstream end of the first sampling pipe 10 to draw the diluted gas mixture at a constant flow rate by suction. A buffer tank for absorbing a pulsed flow component, a flow meter, a processing unit and so on are provided in the pump 11. A valve 12 is arranged in the first sampling pipe 10 in the vicinity of the dilution tunnel 5. A coil heater 13 is arranged directly downstream of the valve 12. A first filter 14 is arranged downstream of the coil heater 13. A temperature detector 15 is arranged directly upstream of the first filter 14. Pressure detectors 16 and 17 are arranged at both sides of the first filter 14. Pressure signals detected by the pressure detectors 16 and 17 are supplied to a first pressure transducer 18 which outputs an electrical signal representing a pressure drop across the filter 14. This signal is supplied to a first processor 19. The processor 19 is also connected to the temperature detector 15 and the first sampling pump 11. The object of the first filter 14 is to collect dry soot. The amount of dry soot collected is estimated in accordance with the pressure drop across the filter 14. Power supplied to the coil heater 13 is adjusted by a slidac 20.

Devices similar to those arranged in the first sampling pipe 10 are arranged downstream of the second sampling pipe 30. A second sampling pump 31 which corresponds to the first sampling pump 11 is positioned at the farthest downstream end. A valve 32 is mounted in a portion of the second sampling pipe 30, in the vicinity of the dilution tunnel 5, and a coil heater 33 is disposed downstream of the valve 32. A second filter 34 is provided farther downstream of the coil heater 33. A temperature detector 35 is arranged upstream of the second filter 34 intervening between pressure detectors 36 and 37. Output signals from the pressure detectors 36 and 37 are supplied to a second pressure transducer 38. The second pressure transducer 38, the second sampling pump 31, and the temperature detector 35 are connected to a second processor 39. A slidac 40 is connected to the coil heater 33.

The above arrangement has a function similar to that provided downstream of the first sampling pipe 10, except that the second filter 34 collects the SOF instead of the dry soot. In order that the second filter 34 can collect only the SOF, an additional filter 41 for collecting the dry soot is disposed in the area upstream of the second filter 34 and directly downstream of the coil heater 33. The additional filter 41 is made from the same material and composition as those of the first filter 14 but has a size several times larger than that of the first filter 14. A relatively long cooling pipe 42 is arranged between the additional filter 41 and the second filter 34.

Figure 2:
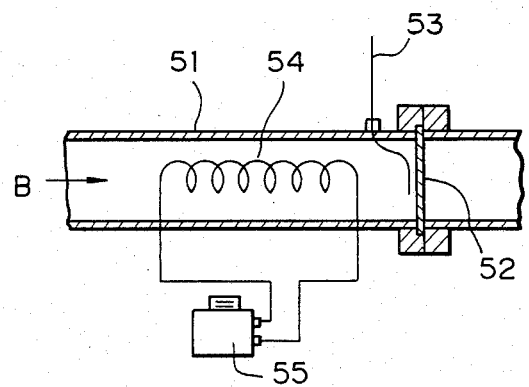
FIG. 2 is a sectional view of a test device for detecting the relationship between the weight of particulates deposited on the filter and the temperature of the gas mixture in front of the filter.

By heating the exhaust gas, the particulates in the exhaust gas can be separated into dry soot and SOF. FIG. 2 shows a test device for determining a relationship between a temperature upsteam of the filter and an amount of particulates collected on the filter. A filter 52 is arranged in a sampling pipe 51, a temperature detector 53 is disposed directly upstream of the filter 52, and a coil heater 54 is arranged upstream of the temperature detector 53. The coil heater 54 is energized by a variable DC power source (slidac) 55. The exhaust gas passes through the filter 52 in the direction indicated by arrow B and is exhausted from the pipe 52. The temperature of the exhaust gas in front of the filter 52 can be varied by adjusting the variable DC power supply 55.

Figure 3:
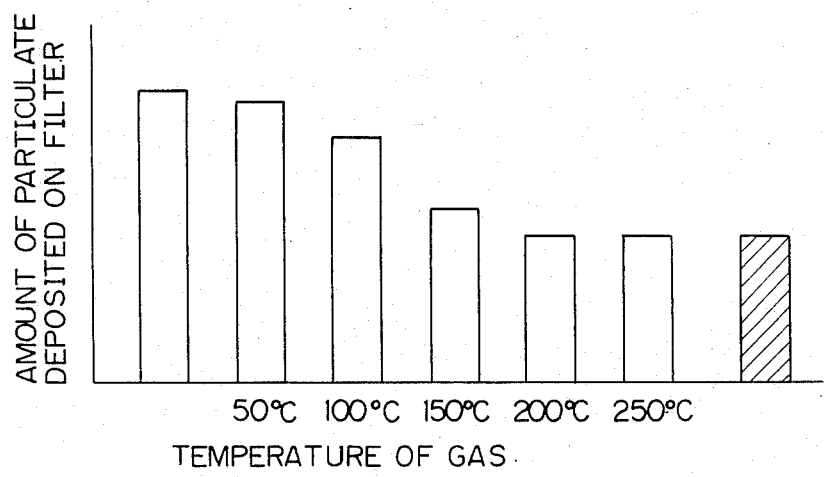
FIG. 3 is a graph showing the relationship between the weight of particulates deposited on the filter and the temperature of the gas mixture in front of the filter.

FIG. 3 is a graph showing the relationship between the temperature of the exhaust gas in front of the filter 52 and the weight of the particulates deposited on the filter 52. A hatched bar in the graph represents the weight of the deposited particulates when the exhaust gas is extracted by dichloromethane in accordance with the Soxhlet extraction method, whereby only dry soot is collected on the filter 52. Other blank bars respectively indicate weights of the particulates deposited on the filter when Soxhlet extraction is omitted. As is apparent from FIG. 3, the amount of particulates deposited is largest when the exhaust gas is not heated by the coil heater 54. When the temperature is increased, the weight of deposited particulates is decreased. When the temperature exceeds 200° C., however, the amount tends to saturate to a value obtained by the application of Soxhlet extraction. This means that only dry soot is collected on the filter 52 but the SOF passes through the filter 52 when the filter is heated at a temperature of 200° C. or higher. Therefore, according to the above heating, the particulates in the exhaust gas can be separated into dry soot and SOF.

The SOF can be collected by a filter after being cooled and condensed in a sampling pipe having a predetermined length. In the embodiment shown in FIG. 1, the cooling pipe 42 is arranged for this purpose.

Figure 4:
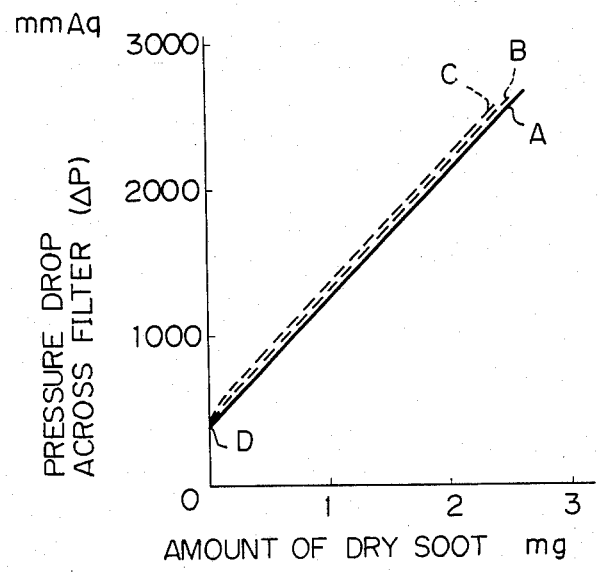
FIG. 4 is a graph showing the amount of dry soot and the pressure drop across the filter.
Figure 5:
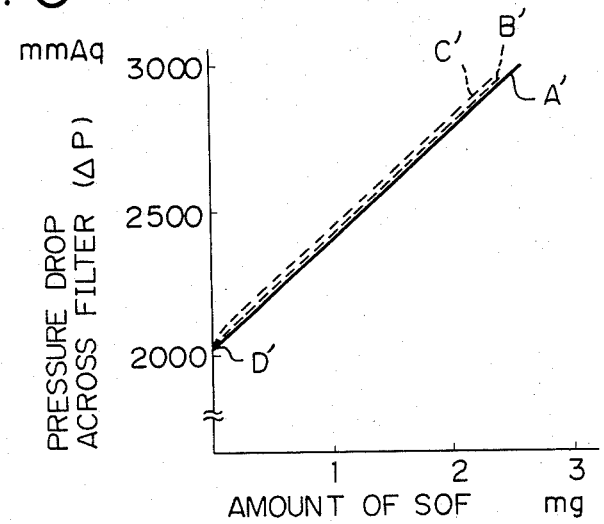
FIG. 5 is a graph showing the amount of SOF and the pressure drop across the filter.

The relationship between the weights of dry soot and SOF collected on the corresponding filters and the pressure drop of the gas mixtures across the corresponding filters is as follows:

According to previous knowledge in the technical field of the present invention, it was believed that the nature of the particulates contained in the exhaust gas may be varied corresponding to the difference of the operating conditions of the engine, and that the vent resistance of the filter may change even if the deposited particulates have the same weight. As shown in FIGS. 4 and 5, however, it has been found that the operating conditions of the engine impart no influence on the nature of the particulates contained in the exhaust gas, both dry soot and SOF, as a result of experiments carried out by the inventors of the present invention. That is, FIGS. 4 and 5 are graphs showing the relationships between the amount of dry soot and a pressure drop $\Delta P$ and between the amount of SOF and the pressure drop $\Delta P$, respectively. Referring to FIGS. 4 and 5, curves A and A', B and B', and C and C' show the relationships between the amounts of particulates and the pressure drops $\Delta P$ when the engine is operated at a low speed of 1,000 rpm, a middle speed of 2,000 rpm, and a high speed of 3,000 rpm, respectively. Reference symbols D and D' represent vent resistances of the filter itself. As is apparent from FIGS. 4 and 5, it is found that the pressure drop $\Delta P$ of the filter is proportional to the amounts of dry soot and SOF and is not substantially influenced by the operating conditions of the engine.

The sampling gas in front of the filter has a temperature of 225° C. in FIG. 4, and 45° C. in FIG. 5. The flow rate of the sampling gas is 20 l/min at 25° C.

By utilizing the filter pressure drop characteristics described above, the amount of dry soot and SOF in the gas varying corresponding to operation modes changing from time to time, i.e., the changing amounts of dry soot and SOF per unit time, can be determined in the following manner:

If the weight of the dry soot or SOF particulates exhausted per unit time is given by W', the weight W' can be given by equation (2) as follows:

$$W' = m \times (Q+q) \qquad (2)$$

where

W': amount of exhausted particulates per unit time (mg/sec), m: weight of particulates in a unit volume sampling gas (mg/m³)

Q: flow rate of the diluted mixture gas blower (m³/sec), and q: flow rate of sampling gas (m³/sec).

Among the physical values included in equation (2), the weight m of particulates in the unit volume sampling gas cannot be calculated in accordance with a conventional method. However, by considering the pressure drop characteristics of the filters 14 and 34 described above, the weight m can be calculated. That is, since the pressure drops of the filters 14 and 34 are proportional to the amounts of collected particulates and to the flow rate, a pressure drop increase d ($\Delta P$) during a very short period of time dt is derived as follows:

$$d(\Delta P) = K \cdot m \cdot q \cdot dt \cdot q \qquad (3)$$

where $\Delta P$: pressure drop (kg/m²),

K: constant determined by a filter diameter or any other factor, and m·q·dt: weight of particulates collected on the filter during the time dt (mg).

Equation (3) can be rewritten as follows:

$$m = \{1/(K \cdot q^2)\} \cdot \{d(\Delta P)\}/dt \qquad (4)$$

where

K: constant determined by the filter diameter or any other factor, and d($\Delta P$)/dt: differential value of the filter pressure drop as a function of time.

The weight m of particulates in the unit volume sampling gas can be calculated in accordance with equation (4). The changing amount of exhausted particulates during operation of the engine can be calculated by using equation (2). The diluted gas mixture blower flow rate Q and the sampling gas flow rate q included in equation (2) are substantially constant during the test and can be regarded as constants.

The differential values of the pressure drops as a function of time are calculated for the filters 14 and 34 and have characteristics proportional to the amount of collected particulates and the sampling gas flow rate. The weights of dry soot and SOF in the unit volume sampling gas can be known. Therefore, the amounts of exhausted dry soot and SOF during the operation of the engine can be obtained.

The operation of the above-mentioned embodiments will now be described.

The valves 12 and 32 are opened upon operation of the engine to be tested. The diluted gas mixture is drawn into the first and second sampling pipes 10 and 30 and is heated by the coil heaters 13 and 33 to a temperature of 200° C. or higher. The heated gas passes through the first filter 14 and the additional filter 41, so that dry soot is collected on the filters 14 and 41. However, the SOF passes through the filters 14 and 41. The SOF particulates having passed through the first filter 14 are collected by a filter (not shown) arranged in the sampling pump 11. The SOF particulates having passed through the additional filter 41 flow through the cooling pipe 42 and are collected by the second filter 34.

The pressure drops of the gas mixtures across each of the first and second filters 14 and 34 are calculated by the first and second pressure transducers 18 and 38, respectively. The output signals from the first and second pressure transducers 18 and 38 are supplied to the first and second processors 19 and 39, respectively. These processors 19 and 39 also receive the signals from the temperature detectors 15 and 35 and the signals (representing the sampling flow rates) from the sampling pumps 11 and 31, respectively. The signals representing the temperatures of the gas mixtures in front of the filters 14 and 34 are utilized for correcting an increase of the pressure drop across each filter due to the increase of the volume and viscosity of the gas caused by the elevated temperature. The relationship between the gas temperature and the increase of the pressure drop caused by this elevated gas temperature is given as $\Delta P = aT + b$ under the conditions of constant mass flow rate. The pressure drops $\Delta P$ are subtracted from the pressure drops calculated by the pressure transducers 18 and 38, respectively, thereby performing the temperature correction. It should be noted that reference symbol T denotes the absolute temperature, and a and b are constants determined by the sampling flow rate and the type of filter, respectively.

The first and second processors 19 and 39 receive the signals described above and calculate the weights of dry soot and SOF in the unit volume sampling gas in accordance with the above-mentioned equations. Therefore, the driver can be informed of the exhaust amounts of dry soot and SOF during the vehicle travel in a real-time manner.

Theoretically, if the first filter 14 and the pressure detectors 16 and 17 are provided in place of the additional filter 41, the dry soot and SOF may be measured by a single sampling pipe. However, in practice, the first filter 14 must be a compact filter having a higher sensitivity for high-precision measurement of the amount of dry soot. When the first filter 14 is used in place of the additional filter 41 shown in FIG. 1, a pressure in the cooling pipe 42 is greatly decreased to increase the flow speed, whereby the pressure drop of the gas mixture across the second filter 34 is increased. The tendency of an increase of the pressure drop varies within the range of from 20 to 30% for individual filters. Correction of such variations exceeds the ability of the processors 19 and 39. In order to prevent this drawback, two sampling pipes are used for separately measuring the dry soot and the SOF in the manner described with reference to the above embodiment. In this regards, when the filter diameter is increased by x times, the pressure drop sensitivity per unit volume is decreased to $1/x^4$.

In the above embodiment, the sampling gas is heated by the coil heaters 13 and 33. However, ribbon heaters surrounding the corresponding sampling pipes may be used in place of the coil heaters 13 and 33. Alternatively, burners may be used for this purpose. When the sampling gas is heated by the coil heaters, heat-insulating material may be installed around the pipes.

Figure 6:
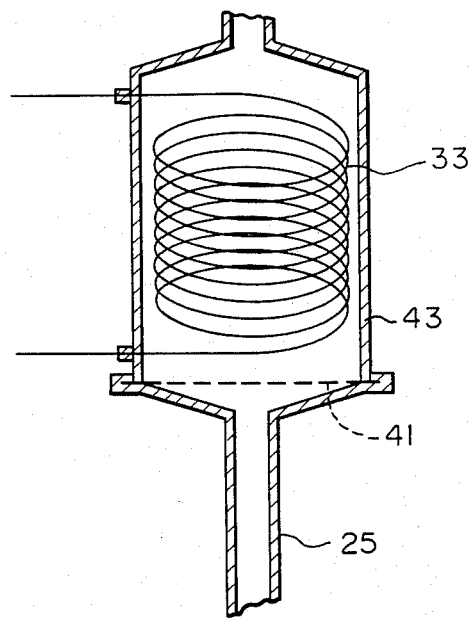
FIG. 6 is a sectional view showing a pipe upstream of the auxiliary pipe and the coil heater according to another embodiment of the present invention.

As shown in FIG. 6, a pipe 43 provided upstream of the additional filter 41 may have the same outer diameter as that of the latter, and a large coil heater 33 having a larger diameter may be arranged in the pipe 43.

We claim:

1. In a system for measuring the amount of particulates of dry soot and soluble organic fractions contained in exhaust gas from an internal combustion engine, comprising a dilution tunnel in which the exhaust gas is mixed with and diluted by a large amount of clean air, a blower means for sucking the exhausted gas and the clean air into said tunnel section and discharging the diluted gas therefrom and means for detecting the amount of particulates in the diluted gas, the improvement in which said means for detecting the amount of particulates in the diluted gas comprises first and second arrangements for detecting the amounts of dry soot and soluble organic fraction, respectively, said first arrangement comprising a first sampling pipe for extracting one part of the diluted gas from said dilution tunnel, a first sampling pump for flowing the diluted gas through said first sampling pipe, a first filter for depositing the dry soot on said first filter, a first heating means disposed in the upstream region in said first sampling pipe for heating the diluted gas taken in said first sampling pipe, a first pressure transducer for converting a value of a pressure drop across said first filter to an electrical signal, and a first processor for calculating the amount of dry soot in the exhaust gas in accordance with a differential value of the pressure drop output from said first pressure transducer as a function of time, while said second arrangement comprising a second sampling pipe for extracting another part of the diluted gas from said dilution tunnel, a second sampling pump for flowing the diluted gas through said second sampling pipe, an additional filter of a relatively large size for depositing dry soot on said additional filter, a second heating means disposed in the upstream region in said second sampling pipe for heating the diluted gas taken in said second sampling pipe, a second filter disposed downstream of said additional filter for depositing the soluble organic fraction on said second filter, a second pressure transducer for converting a value of a pressure drop across said second filter to an electrical signal, and a second processor for calculating the amount of soluble organic fraction in the exhaust gas in accordance with a differential value of the pressure drop output from said second pressure transducer as a function of time.

2. A system according to claim 1, in which a cooling pipe is provided between said additional filter and said second filter for condensing the soluble organic fraction in said second arrangement.

3. A system according to claim 1, in which temperature detecting means are provided directly upstream of said first and second filters, respectively, for correcting the pressure drops across said first and second filters caused by the heating of the diluted gas.

* * * * *